(12) United States Patent
Mitschke et al.

(10) Patent No.: US 7,519,415 B2
(45) Date of Patent: Apr. 14, 2009

(54) METHOD AND APPARATUS FOR IMAGE SUPPORT OF AN OPERATIVE PROCEDURE IMPLEMENTED WITH A MEDICAL INSTRUMENT

(75) Inventors: Matthias Mitschke, Walnut Creek, CA (US); Sorin-Alexandru Neagu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 550 days.

(21) Appl. No.: 11/015,169

(22) Filed: Dec. 17, 2004

(65) Prior Publication Data
US 2005/0163279 A1    Jul. 28, 2005

(30) Foreign Application Priority Data
Dec. 19, 2003    (DE)    ............... 103 60 025

(51) Int. Cl.
A61B 5/00    (2006.01)
(52) U.S. Cl. ............ 600/424; 600/427; 702/150
(58) Field of Classification Search ............... 600/424, 600/427, 429; 702/94–95, 150–153; 128/899
See application file for complete search history.

(56) References Cited

U.S. PATENT DOCUMENTS

| | | | |
|---|---|---|---|
| 5,772,594 A * | 6/1998 | Barrick | 600/407 |
| 5,951,571 A | 9/1999 | Audette | |
| 6,006,126 A | 12/1999 | Cosman | |
| 6,016,439 A | 1/2000 | Acker | |
| 6,050,724 A * | 4/2000 | Schmitz et al. | 378/205 |
| 6,259,943 B1 * | 7/2001 | Cosman et al. | 600/429 |
| 6,317,621 B1 | 11/2001 | Graumann et al. | |
| 6,359,959 B1 * | 3/2002 | Butler et al. | 378/20 |
| 6,466,638 B1 * | 10/2002 | Silver et al. | 378/4 |
| 6,527,443 B1 | 3/2003 | Vilsmeier et al. | |
| 6,720,966 B2 | 4/2004 | Barth et al. | |
| 6,782,287 B2 * | 8/2004 | Grzeszczuk et al. | 600/424 |
| 6,795,571 B2 | 9/2004 | Kusch | |
| 6,851,855 B2 * | 2/2005 | Mitschke et al. | 378/207 |
| 6,856,827 B2 * | 2/2005 | Seeley et al. | 600/426 |
| 6,932,506 B2 * | 8/2005 | Mitschke et al. | 378/207 |
| 6,947,786 B2 * | 9/2005 | Simon et al. | 600/427 |
| 7,050,844 B2 * | 5/2006 | Strobel | 600/424 |

(Continued)

FOREIGN PATENT DOCUMENTS

WO    WO 96/10949    4/1996

*Primary Examiner*—Ruth S Smith
*Assistant Examiner*—Jonathan G Cwern
(74) *Attorney, Agent, or Firm*—Schiff Hardin LLP

(57) ABSTRACT

In a method and apparatus for image support of an operative procedure implemented with a medical instrument, a two-dimensional x-ray image of a volume region to be treated is generated and stored with a C-arm x-ray apparatus in at least one pivot position of the C-arm. With a position detection device, the position of an apparatus reference system and the position of a reference system in the image generation are at least indirectly detected. Between the reference system and an image coordinate system of the x-ray image, a transformation rule is determined using known, apparatus-specific mapping rules that are measured and stored in a preceding calibration. During the subsequent procedure, with the position detection device the position of an instrument reference system is detected in the reference system and the instrument is mixed into the stored two-dimensional x-ray image with accurate position by means of this transformation rule.

12 Claims, 3 Drawing Sheets

U.S. PATENT DOCUMENTS

| | | | |
|---|---|---|---|
| 7,068,752 B2* | 6/2006 | Brandt | 378/62 |
| 2001/0036245 A1* | 11/2001 | Kienzle et al. | 378/4 |
| 2001/0053204 A1* | 12/2001 | Navab et al. | 378/205 |
| 2002/0044631 A1* | 4/2002 | Graumann et al. | 378/205 |
| 2002/0077543 A1* | 6/2002 | Grzeszczuk et al. | 600/424 |
| 2003/0073901 A1* | 4/2003 | Simon et al. | 600/424 |
| 2003/0088179 A1* | 5/2003 | Seeley et al. | 600/424 |
| 2003/0130576 A1 | 7/2003 | Seeley et al. | |
| 2003/0219102 A1* | 11/2003 | Mitschke et al. | 378/207 |
| 2004/0008809 A1* | 1/2004 | Webber | 378/8 |
| 2004/0013240 A1* | 1/2004 | Mitschke et al. | 378/205 |
| 2004/0138548 A1* | 7/2004 | Strommer et al. | 600/407 |
| 2004/0152970 A1* | 8/2004 | Hunter et al. | 600/424 |
| 2004/0152972 A1* | 8/2004 | Hunter | 600/424 |
| 2004/0171924 A1* | 9/2004 | Mire et al. | 600/407 |
| 2004/0199072 A1* | 10/2004 | Sprouse et al. | 600/424 |
| 2005/0004449 A1* | 1/2005 | Mitschke et al. | 600/424 |
| 2005/0059886 A1* | 3/2005 | Webber | 600/426 |
| 2005/0085714 A1* | 4/2005 | Foley et al. | 600/424 |
| 2005/0085715 A1* | 4/2005 | Dukesherer et al. | 600/424 |
| 2005/0085720 A1* | 4/2005 | Jascob et al. | 600/424 |
| 2005/0105694 A1* | 5/2005 | Brandt | 378/210 |
| 2005/0107688 A1* | 5/2005 | Strommer | 600/424 |
| 2005/0117708 A1* | 6/2005 | Cho et al. | 378/164 |
| 2005/0163279 A1* | 7/2005 | Mitschke et al. | 378/62 |
| 2005/0165292 A1* | 7/2005 | Simon et al. | 600/407 |
| 2005/0273004 A1* | 12/2005 | Simon et al. | 600/424 |
| 2006/0015030 A1* | 1/2006 | Poulin et al. | 600/424 |
| 2007/0100258 A1* | 5/2007 | Shoham et al. | 600/587 |

* cited by examiner

METHOD AND APPARATUS FOR IMAGE SUPPORT OF AN OPERATIVE PROCEDURE IMPLEMENTED WITH A MEDICAL INSTRUMENT

BACKGROUND OF THE INVENTION

1. Field of the Invention

The present invention concerns a method and an apparatus for image support of an operative procedure implemented with a medical instrument.

2. Description of the Prior Art

In the implementation of an operative procedure on a living subject, it is known to support the surgeon in the guiding of the medical instrument with optical image information. For this, an image of the instrument is mixed into a 2D or 3D image (acquired, for example, with an x-ray apparatus) of the treatment area of the subject.

In order to enable the implementation of such an intraoperative navigation, also known as fluoronavigation, a 2D x-ray image, for example of the treatment area, can be continuously created during the operative procedure, such that the instrument is imaged by the x-ray radiation together with the treatment area. Due to the high radiation stress with such a continual x-ray exposure, this is disadvantageous both for the treated individual and for the treatment personnel. To prevent such a high radiation exposure, it is known to temporally decouple the x-ray image generation and the operative procedure and to navigate the surgical instrument by means of a camera after a successful x-ray image generation, with an image of the instrument being mixed with correct position in real time into an existing (i.e. previously acquired) x-ray image. For this purpose, it is necessary to determine both the position of the instrument in a reference system and the position of this reference system relative to the image coordinates of the x-ray image.

The x-ray apparatus normally used for intraoperative navigation is in many cases a C-arm x-ray apparatus, in which the x-ray source and the x-ray receiver are mounted opposite one another on a C-arm that is pivotable around two axes relative to one another, in order to be able to generate x-ray images from different projection directions.

For the positionally precise mixing of an instrument, whose spatial position is known in a reference system, into a 2D x-ray image, precise knowledge of the spatial position of the projection cone belonging to this 2D image in this reference system is necessary. Ideally, the position of this projection cone is already known when the spatial position of the image plane, i.e. the entrance surface of the x-ray receiver, is fixed, such that it should be sufficient to determine the position of the x-ray receiver in the reference system in which the position of the instrument is also detected. In practice, however, it has proven to be the case that determination of the position of the x-ray receiver alone is not sufficient in order to be able to safely establish the projection cone, since this does not always exhibit the same relative position relative to the x-ray receiver due to the unavoidable deflection (distortion) of the C-arm dependent on the position of the x-ray axis.

In German OS 199 17 867, it is proposed to arrange on the x-ray receiver a reference structure that, in addition to optical position markers for camera-aided navigation, also has x-ray markers that lie in the beam path of the x-ray radiation and are imaged in the x-ray image. The precise position of the projection cone can be calculated and eventual distortions can also be eliminated by calculation from the position of the x-ray markers visible in the x-ray image.

The x-ray markers that are visible in the x-ray image have the disadvantage that they shadow a part of the x-ray image and in this manner are unavoidably associated with an information loss. This information loss cannot be completely prevented even when these x-ray markers are eliminated from the x-ray image by digital image processing.

SUMMARY OF THE INVENTION

An object of the present invention is to provide a method for image support of an operative procedure implemented with a medical instrument, which enables a precise navigation without the use of x-ray markers. It is also an object of the present invention to provide an apparatus operating according to this method.

The first object is achieved according to the invention by a method for image support of an operative procedure implemented with a medical instrument, wherein a two-dimensional x-ray image of a volume region to be treated is generated with a C-arm x-ray apparatus in at least one pivot position of the C-arm, and the image is stored. With a position detection device, the position of an apparatus reference system and the position of a reference system existing in the image generation is at least indirectly detected. A transformation rule is determined between the reference system and an image coordinate system of the x-ray image using known, apparatus-specific rules measured and stored in a preceding calibration. During the subsequent procedure, with the position detection device the position of an instrument reference system (associated with the instrument) is detected in the reference system, and the instrument is mixed into the stored two-dimensional x-ray image with accurate position using the determined transformation rule.

By means of these measures it is possible to mix the medical instrument into a previously acquired two-dimensional x-ray image with accurate position without requiring the application of additional x-ray markers that can impair the image quality. Moreover, with this procedure a correct mixing of the instrument into the x-ray image is also possible when the position detection device is moved into another position in space during the procedure, for example for better detection capability of the instrument.

In a preferred embodiment of the method, for determination of the transformation rule the following steps are implemented between the image coordinate system and the reference system:

a) detection of the position of the C-arm x-ray apparatus with the position detection device in a starting position, b) determination, with the aid of the position data of the C-arm x-ray apparatus detected in the preceding step, of a transformation rule between the navigation reference system and an apparatus reference system associated with the C-arm x-ray apparatus, c) determination of a transformation rule between the reference system and the apparatus reference system, d) determination, with the aid of a projection matrix associated with a pivot position and determined and stored in a preceding calibration, of a transformation rule between the apparatus reference system and the image coordinate system of the two-dimensional x-ray image generated in this pivot position, e) determination of the transformation rule between the reference system and the image coordinate system with the aid of the transformation rules determined in both of the preceding steps.

By the use of the mapping rule (designated as a projection matrix), that is known and apparatus-specific for the appertaining C-arm x-ray apparatus for a number of positions of the C-arm, between the apparatus reference system and the image coordinate system, a correct navigation is possible with minimal calibration effort.

In a further embodiment of the invention, the position of the C-arm x-ray apparatus in an initial position of the C-arm is detected using position markers that are disposed on the x-ray receiver. With a mapping rule determined in a preceding calibration, the position of the apparatus reference system is determined from the position of a receiver reference system associated with these position markers. By the use of a mapping rule between the receiver reference system and the apparatus reference system (designated as an apparatus matrix and determined only one time and apparatus-specifically for each C-arm x-ray apparatus), the position of the apparatus reference system can be particularly simply and precisely determined.

In another embodiment of the method, the actual pivot position of the C-arm is detected, and that projection matrix that has been determined and stored in a calibration for a calibration position, which will be next after the current pivot position, is associated with this pivot position.

The position of a base reference system that is stationary in space is detected with the position detection device to determine the transformation rule between the navigation reference system and the apparatus reference system. By means of this procedure it is possible to move the position detection device into arbitrary positions in treatment space after the determination of the transformation rule between the navigation reference system and the apparatus reference system.

The second object is achieved according to the invention by an apparatus for image support of an operative procedure implemented with a medical instrument, having a C-arm x-ray apparatus to generate a two-dimensional x-ray image; a position detection device to at least indirectly detect the position of an apparatus reference system associated with the C-arm x-ray apparatus; a reference system associated with the patient and an instrument reference system associated with the medical instrument; a computer to determine a transformation rule (valid during the generation of the x-ray image) between the reference system and an image coordinate system using stored apparatus-specific imaging rules, as well as to determine a transformation rule (valid during the procedure) between the reference system and the instrument reference system, and for positionally accurate mixing of the instrument into the two-dimensional x-ray image using these transformation rules.

Embodiments of the apparatuses track the above-described embodiments of the method with corresponding advantages.

DESCRIPTION OF THE PREFERRED EMBODIMENTS

Figure 1:
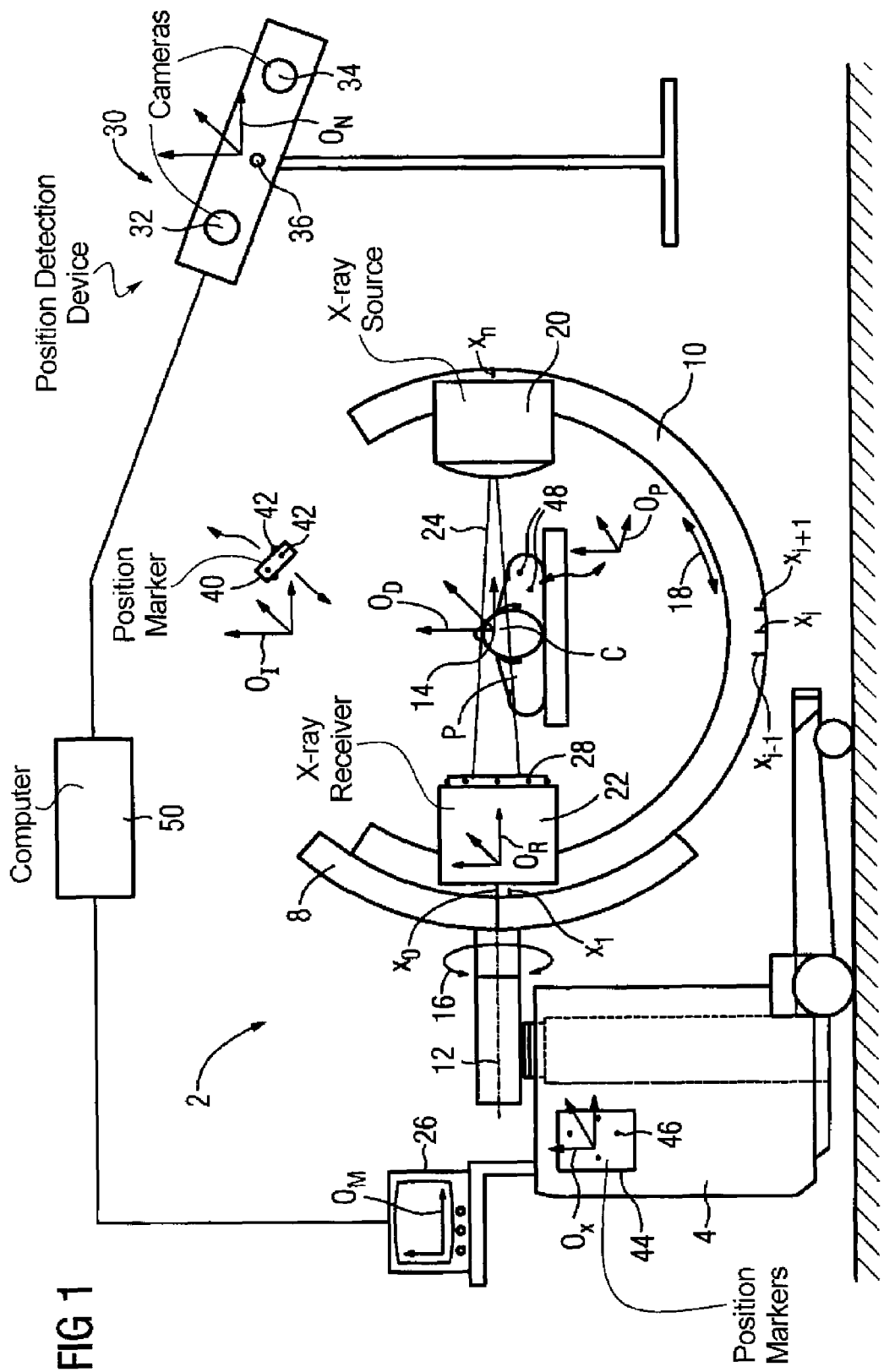
FIGS. 1 and 2 show an apparatus according to the invention respectively in a starting position and an operating position.

As shown in FIG. 1, an apparatus according to the invention has a mobile C-arm x-ray apparatus 2 with an apparatus cart 4 on which a support 8 for the C-arm 10 is mounted in a height-adjustable manner. The support 8 is pivotable around an axis 12 (angulation axle) oriented parallel to the plane of the drawing. In the support 8, the C-arm is guided such that it can pivot around an axis 14 (orbital axis) perpendicular to the plane of the drawing. The pivot movements made possible by this support 8 are illustrated by the double arrows 16 and 18.

An x-ray source 20 and an x-ray receiver 22 are disposed opposite one another on the C-arm 10. A patient P to be treated is located in the beam cone 24 of the x-ray radiation emitted by the x-ray source 20.

The C-arm x-ray apparatus 2 has a display 26 for reproduction of a two-dimensional x-ray image acquired by the x-ray receiver 22. A two-dimensional image coordinate system OM is associated with the x-ray apparatus.

A system component of the C-arm x-ray apparatus 2 (in the exemplary embodiment the x-ray receiver 22) is provided with optical position markers 28, for example IR reflectors, for position detection. These establish a receiver reference system $O_R$.

In the region of the C-arm x-ray apparatus 2, a mobile position detection device 30 is arranged that has two cameras 32 and 34 (in the example these are infrared cameras) as well as an infrared transmitter 36. As an alternative, the use of a position detection device that is stationary in the treatment space is also possible. A navigation reference system $O_N$, to which the coordinates or position data of the system components detected by the position detection device 30 are referenced, is associated with the position detection device 30.

Moreover, a medical instrument 40 is illustrated in FIG. 1 that is likewise provided with optical position markers 42 with which a determination of its position, i.e. the position of an instrument reference system $O_I$ defined by these position markers 42, is enabled with the position detection device 30.

In a first step, the apparatus cart 4 with the C-arm x-ray apparatus 2 is moved into an operating position in the treatment space and there is locked, such that the C-arm x-ray apparatus 2 is fixed stationary in the treatment space at least during the entire duration of a calibration and subsequent image generation.

An apparatus reference system $O_D$, whose position in space, independent of the current angle position of the C-arm, defines a basic position of the C-arm x-ray apparatus 2 given a stationary fixed apparatus cart 4, is associated with the C-arm x-ray apparatus 2. In the exemplary embodiment, the origin of this apparatus reference system $O_D$ lies at a point known as the isocenter, i.e. the intersection point of the angulation axis 12 with the orbital axis 14. The x-axis and y-axis of the apparatus reference system $O_D$ respectively proceed parallel to the angulation axis 12 and the orbital axis 14.

A marker plate 44 with position markers 46 is arranged on the apparatus cart 4. These establish a base reference system $O_X$ that is stationary in space given a fixed apparatus cart 4. Such a stationary base reference system $O_X$ alternatively can be associated with a different position that is fixed in the treatment space.

Since it is possible that the treatment area may shift during the subsequent procedure, a dynamic reference system $O_P$ is established by position markers 44 that are disposed near the operative body part to be treated, for example on a marker plate that is mounted so as to be fixed on a bone.

The calculation operations necessary for correct navigation are executed in a computer 50 in which the apparatus-specific data (apparatus matrix, projection matrices) of the C-arm x-ray apparatus 2 are also stored.

To determine the position of the apparatus reference system $O_D$, given a stationary apparatus cart 4, the C-arm 10 is pivoted into a starting position $x_0$. In this (in the exemplary embodiment, horizontal) starting position $x_0$, a transformation rule $\underline{T}_{NR,0}$ between the navigation reference system $O_N$ and a receiver reference system $O_R$ associated with the x-ray receiver 22 is determined using the position detection device 30 and the optical position markers 28 on the x-ray receiver 22.

For this starting position $x_0$, the transformation rule (designated as apparatus matrix $\underline{\underline{M}}_{40}$) between the apparatus reference system $O_D$ and the receiver reference system $O_R$ associated with the x-ray receiver 22 is determined in a preceding calibration event and has been stored in the computer 50. The transformation rule between the navigation reference system $O_N$ and the apparatus reference system $O_D$, i.e. the position of the apparatus reference system $O_D$ in the navigation reference system $O_N$, is thereby also known.

In order to also have knowledge about the spatial position of the apparatus reference system $O_D$ in the navigation reference system $O_N$ position of the detection device 30 when its position is subsequently changed relative to the fixed apparatus cart, during the calibration of the position detection device 30 the position of the stationary base reference system $O_X$ is detected during the entire calibration and image generation phase, i.e. a transformation rule $\underline{\underline{T}}_{NX,0}$ between the navigation reference system $O_N$ and a stationary base reference system $O_X$ is determined. The index "O" indicates that it concerns events during the calibration. In the exemplary embodiment, the base reference system $O_X$ is fixed on the apparatus cart 4, since this remains stationary at least until the conclusion of the image generation, normally even during the entire procedure.

The transformation rules $\underline{\underline{T}}_{XR,0}$ and $\underline{\underline{T}}_{XD}$ between the base reference system $O_X$ and the receiver reference system $O_R$ and the apparatus reference system $O_D$ $$\underline{\underline{T}}_{XR,0} = \underline{\underline{T}}_{NX,0}^{-1} * \underline{\underline{T}}_{NR,0} \text{ and } \underline{\underline{T}}_{XD} = \underline{\underline{T}}_{XR,0} * \underline{\underline{M}}_{40}$$

thus can be calculated. The calibration is concluded.

Figure 3:
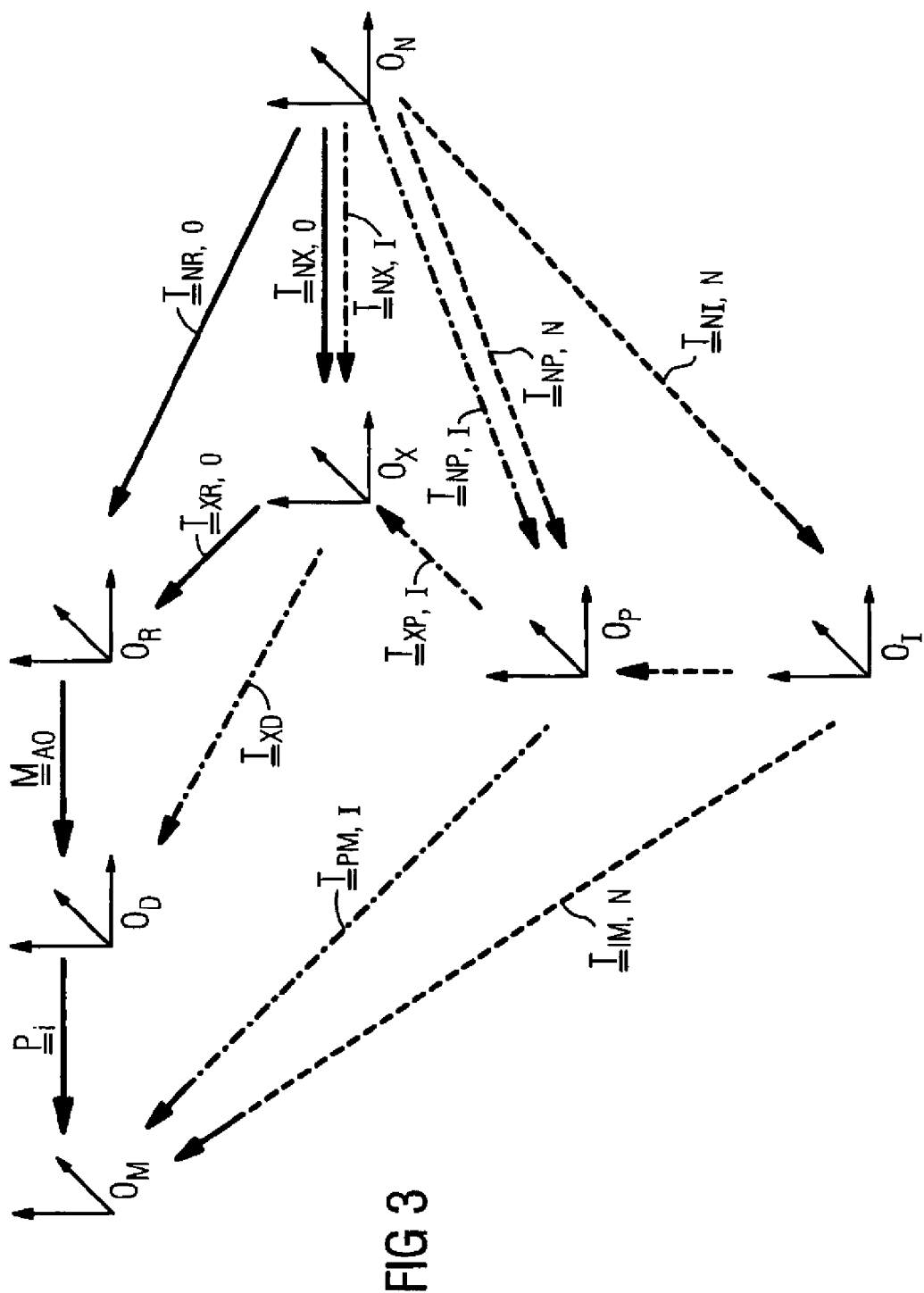
FIG. 3 is a schematic representation of a procedure with image-supported navigation according to the invention.

The steps executed during the calibration are illustrated in FIG. 3 using the solid arrows.

The use of the stationary base reference system $O_X$ has the advantage that the surgeon can subsequently (i.e. in the subsequent image generation) bring the position detection device 30 into a different position, for example a position that is more advantageous for detection of the position markers 28 on the x-ray receiver 22.

Subsequent to the calibration, the C-arm 10 is pivoted into a freely selectable pivot position in which an x-ray image of the treatment area is generated. In this operating position, the position of the base reference system $O_X$ (i.e. the transformation rule $\underline{\underline{T}}_{NX,I}$ between the navigation reference system $O_N$ and the base reference system $O_X$) is determined by the position detection device 30, whose location no longer has to coincide (due to the use of the base reference system $O_X$) with its location during the calibration. The index "I" designates events during the image generation.

Figure 2:
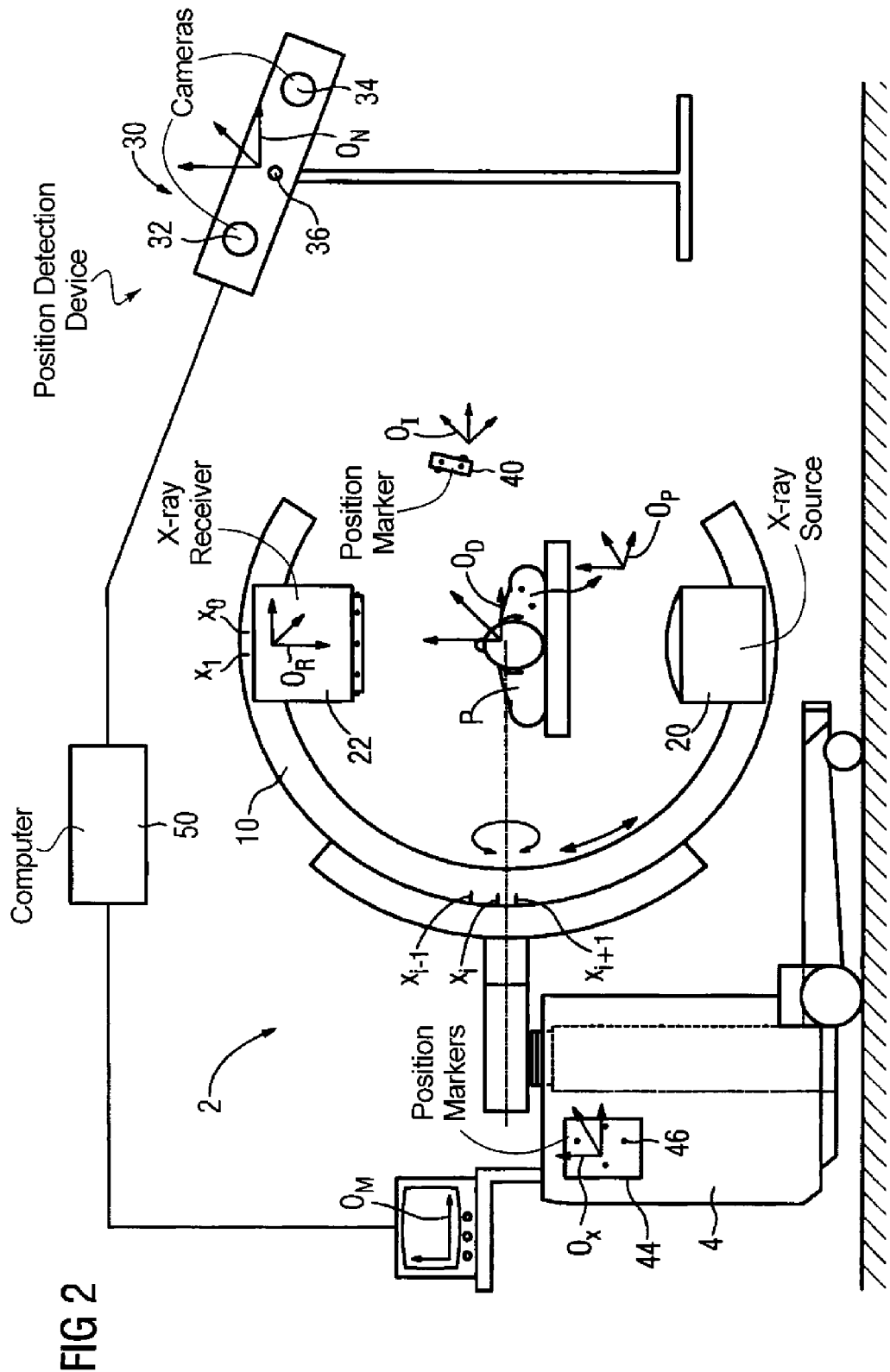

This is shown in FIG. 2, in which the pivot position of the C-arm 10 is located between the calibration positions $x_i$ and $x_{i+1}$. Each calibration position $x_i$ corresponds to an angle pair made up of an angulation angle and an orbital angle (in the Figure, a situation for the angulation angle=0 is shown simplified, such that the calibration positions $x_i$ differ only in the orbital angles). For each of these calibration positions $x_i$, in a preceding, one-time, apparatus-specific calibration measurement an associated projection matrix $\underline{\underline{P}}_i$ has been determined and stored in the computer 50, with which the apparatus reference system $O_D$ is correctly projected in the image coordinate system $O_M$, namely $$\underline{\underline{P}}_i: O_D \rightarrow O_M$$

For the projection matrix $\underline{\underline{P}}$ that is necessary in the pivot position for correct reproduction of the position of the apparatus reference system $O_D$ in the image coordinate system $O_M$, any projection matrix is used that belongs to a calibration position that will be next after the current pivot position is used. In the exemplary embodiment, this is the calibration position $x_i$ and, correspondingly, the projection matrix $\underline{\underline{P}}_i$. The actual pivot position of the C-arm 10 is detected in the exemplary embodiment by suitable angle transmitters on the C-arm x-ray apparatus 2. As an alternative, the current pivot position of the C-arm 10 can be determined with the position detection device 30, by detecting the actual position of the x-ray receiver 22 and from this determining (with the aid of the position detection device) a transformation rule $\underline{\underline{T}}_{XR}$ between the base reference system $O_X$ and the current receiver reference system $O_R$. The rotation angle can then be calculated and the associated projection matrix of the next pivot position can then be determined from the transformation rule $\underline{\underline{T}}_{XR}$ and the transformation rule $\underline{\underline{T}}_{XR0}$ determined in the initial position $x_0$.

In the pivot position, the position of the reference system $O_P$, i.e. the transformation rule $\underline{\underline{T}}_{NP,I}$ between the navigation reference system $O_N$ and the reference system $O_P$, is determined by the position detection device 30. The transformation rule $$\underline{\underline{T}}_{XP,I} = \underline{\underline{T}}_{XN,I} * \underline{\underline{T}}_{NP,I}$$

between the base reference system $O_X$ and the reference system $O_P$, and thus also the transformation rule $$\underline{\underline{T}}_{PD,I} = \underline{\underline{T}}_{XP,I}^{-1} * \underline{\underline{T}}_{XD}$$

between the reference system $O_P$ and the apparatus reference system $O_D$ are thus also known, such that (with the aid of the projection matrix $\underline{\underline{P}}_i$) the reference system $O_P$ can be correctly projected in the image coordinate system $O_M$. There is then a fixed transformation relation $\underline{\underline{T}}_{PM,I} = \underline{\underline{T}}_{PD,I} * \underline{\underline{P}}_i$ between the image coordinate system $O_M$ and the reference system $O_P$. In other words: if the coordinates of a spatial point $(y_{p1}, y_{p2}, y_{p3})$ are in a reference system known, its coordinates $(y_{M1}, y_{M1})$ are fixed in the image coordinate system $O_M$. The steps executed in the image generation are illustrated in FIG. 3 by dash-dot arrows.

In this manner, a number of x-ray images acquired from different projection directions, with respective known transformation rule between the image reference system and the reference system valid at the point in time of the image generation, can be generated and stored.

After the acquisition of the at least one x-ray image, the actual navigation is begun. For this, the position detection device 30 can be moved into a position advantageous for the detection capability of the position markers 42 arranged on the instrument. Now both the position of the instrument reference system $O_i$ and the dynamic reference system $O_P$ are detected with the position detection device 30 in the navigation reference system $O_N$, or the transformation rules $\underline{\underline{T}}_{NI,N}$ and $\underline{\underline{T}}_{NP,N}$ are detected, from which the transformation rule $$\underline{\underline{T}}_{IP,N} = \underline{\underline{T}}_{NI,N}^{-1} * \underline{\underline{T}}_{NP,N}$$

is determined, wherein the index "N" designates method steps that occur during the navigation. This now indicates the position of the instrument 40 in the reference system $O_P$ whose position is in turn known in the image coordinate system $O_M$, such that the position of the instrument 40 can be correctly projected in the image with the aid of the transformation rule $$\underline{\underline{T}}_{IM,N} = \underline{\underline{T}}_{IP,N} * \underline{\underline{T}}_{PM,I}$$

These steps are illustrated in FIG. 3 by the dashed arrows.

During the navigation, it is in principle possible to remove the C-arm x-ray apparatus 2 in order, in this manner, to enable an unhindered access to the treatment area for the surgeon. However, leaving the apparatus cart 6 in a position that is locked during the calibration has the advantage that it is possible for the surgeon to generate a new x-ray image from a position more advantageous for the next operation without recalibration.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for conducting an image-supported surgical procedure implemented with a medical instrument having an instrument reference associated therewith, comprising the steps of:

with an x-ray apparatus having a C-arm on which a radiation source and a radiation receiver are mounted, obtaining a two-dimensional x-ray image of a volume, in which a surgical procedure is to be implemented, of a living subject with the C-arm in at least one pivot position, and storing said two-dimensional x-ray image, said two-dimensional x-ray image having an image coordinate system associated therewith;

with a freely moveable position detection device in a first position, detecting a position of a base reference system, that is stationary in space during acquisition of said two-dimensional x-ray image, said position detection device having a field of view;

in a calibration procedure executed in a computer, determining a transformation rule between said base reference system and said image coordinate system of the two-dimensional x-ray image using rules specific to said x-ray apparatus that are acquired and stored in the calibration procedure; and during said surgical procedure conducted subsequent to said calibration procedure, placing said position detection device in a second position that is arbitrarily selectable relative to said first position to best encompass an instrument in said field of view that is used to implement said surgical procedure and, with said position detection device in said second position detecting, a position of the instrument reference, and in said computer, identifying the position of the instrument reference within said base reference system, and, using said transformation rule in said computer, mixing a representation of said instrument into the stored two-dimensional x-ray image with an accurate position to produce a mixed x-ray image available for visual display.

2. A method as claimed in claim 1 wherein said position detection device has a navigation reference system associated therewith and wherein said x-ray apparatus has an apparatus reference system associated therewith, and comprising the steps of:

detecting a position of the C-arm of the x-ray apparatus in a starting position with said position detection device in said first position;

in said computer, determining, using the position of the C-arm in said starting position, a transformation rule between said navigation reference system and the apparatus reference system;

in said computer, determining a transformation rule between the base reference system and the apparatus reference system;

in said calibration procedure, detecting and storing said at least one pivot position of said C-arm;

determining, using a projection matrix associated with said at least one pivot position that was acquired and stored in said calibration procedure, a transformation rule between said apparatus reference system and said image coordinate system at said at least one pivot position; and in said computer, determining the transformation rule between the base reference system and the image coordinate system using said transformation rule between the navigation reference system and the apparatus reference system and the transformation rule between the base reference system and the apparatus reference system and the transformation rule between the apparatus reference system and the image coordinate system.

3. A method as claimed in claim 2 comprising, while said position detection device is in said first position, detecting the position of the C-arm using position markers disposed on the radiation receiver that define a receiver reference system, and, in said computer, determining an apparatus matrix in said calibration procedure and, using said apparatus matrix, determining the position of the apparatus reference system from the position of the receiver reference system.

4. A method as claimed in claim 2 comprising detecting an actual pivot position of the C-arm in said starting position and, in said computer, determining said projection matrix and storing said projection matrix in said calibration procedure for a calibration position that will occur next after said actual pivot position.

5. A method as claimed in claim 2 comprising moving said position detection device to said second position after determining said transformation rule between said navigation reference system and said apparatus reference system.

6. A method as claimed in claim 1 comprising visually displaying said mixed x-ray image.

7. An apparatus for conducting an image-supported surgical procedure implemented with a medical instrument, comprising:

a medical instrument having an instrument reference system associated therewith;

an x-ray apparatus having a C-arm on which a radiation source and a radiation receiver are mounted, for obtaining a two-dimensional x-ray image of a volume, in which a surgical procedure is to be implemented with said medical instrument, of a living subject with the C-arm in at least one pivot position;

a memory in which said two-dimensional x-ray image is stored, said two-dimensional x-ray image having an image coordinate system associated therewith;

a freely moveable position detection device having a field of view, said position detecting device, while in a first position, detecting a position of a stationary base reference system during acquisition of said two-dimensional x-ray image;

a computer that determines a transformation rule between said base reference system and said image coordinate system of the two-dimensional x-ray image using rules specific to said x-ray apparatus that are acquired and stored in a calibration procedure;

with said position detection device placed in a second position that is arbitrarily selectable relative to said first position to best encompass said medical instrument in said field of view, detecting, during said surgical procedure conducted subsequent to said calibration procedure, a position of said instrument reference and, in said computer, identifying the position of the instrument reference within said base reference system; and said computer using said transformation rule, mixing a representation of said instrument into the stored two-dimensional x-ray image with an accurate position to produce a mixed x-ray image available for visual display.

8. An apparatus as claimed in claim 7 wherein said position detection device has a navigation reference system associated therewith, and acquires and stores said at least one pivot position of said C-arm in said calibration procedure and wherein said x-ray apparatus has an apparatus reference system associated therewith, and wherein:

said position detection device, while in said first position detects a position of the C-arm of the x-ray apparatus in a starting position;

and wherein said computer determines, using the position of the C-arm in said starting position, a transformation rule between said navigation reference system and the apparatus reference system, determines a transformation rule between the base reference system and the apparatus reference system, determines, using a projection matrix associated with said at least one pivot position that was acquired and stored in said calibration procedure, a transformation rule between said apparatus reference system and said image coordinate system at said pivot position, and determines the transformation rule between the base reference system and the image coordinate system using said transformation rule between the navigation reference system and the apparatus reference system and the transformation rule between the base reference system and the apparatus reference system and the transformation rule between the apparatus reference system and the image coordinate system.

9. An apparatus as claimed in claim 8 wherein the position detection device detects the position of the C-arm in said starting position using position markers disposed on the radiation receiver that define a receiver reference system, and wherein said computer determines an apparatus matrix in said calibration procedure and, using said apparatus matrix, determines the position of the apparatus reference system from the position of said receiver reference system.

10. An apparatus as claimed in claim 9 wherein said computer is configured to determine said transformation rule between said navigation reference system and said apparatus reference system before said position detection device is moved to said second position.

11. An apparatus as claimed in claim 8 wherein said position detection device, while in said first position, detects an actual pivot position of the C-arm in said starting position and wherein said computer determines said projection matrix and stores said projection matrix in said calibration procedure for a calibration position that will occur next after said actual pivot position.

12. An apparatus as claimed in claim 7 comprising a display at which said computer causes said mixed x-ray image to be visually displayed.

* * * * *